United States Patent
Wai

(10) Patent No.: US 10,151,076 B2
(45) Date of Patent: Dec. 11, 2018

(54) APPARATUS FOR BI-DIRECTIONAL LOAD TESTING OF DRIVEN PILES AND INJECTION PILES, AND METHOD THEREOF

(71) Applicant: WILL N WELL PROPERTY SDN BHD, Negeri Sembilan (MY)

(72) Inventor: Yee Kong Wai, Kuala Lumpur (MY)

(73) Assignee: WILL N WELL PROPERTY SDN BHD (MY)

( * ) Notice: Subject to any disclaimer, the term of this patent is extended or adjusted under 35 U.S.C. 154(b) by 252 days.

(21) Appl. No.: 15/121,830

(22) PCT Filed: Jan. 30, 2015

(86) PCT No.: PCT/MY2015/000007
§ 371 (c)(1),
(2) Date: Aug. 26, 2016

(87) PCT Pub. No.: WO2015/130158
PCT Pub. Date: Sep. 3, 2015

(65) Prior Publication Data
US 2017/0073922 A1    Mar. 16, 2017

(30) Foreign Application Priority Data
Feb. 26, 2014   (MY) ................. PI 2014000539

(51) Int. Cl.
*G01N 3/00*       (2006.01)
*E02D 33/00*      (2006.01)
(Continued)

(52) U.S. Cl.
CPC .............. *E02D 33/00* (2013.01); *E02D 7/02* (2013.01); *G01N 3/10* (2013.01);
(Continued)

(58) Field of Classification Search
CPC .......... E02D 33/00; E02D 1/022; E02D 7/02; E02D 2600/10; G01N 2203/0042; G01N 3/10
See application file for complete search history.

(56) References Cited

U.S. PATENT DOCUMENTS

| 5,608,169 A | 3/1997 | Fujioka et al. | |
| 7,905,150 B2 * | 3/2011 | Kranzmann | G01N 3/02 73/40 |

(Continued)

FOREIGN PATENT DOCUMENTS

KR    100914058 B1    8/2009

OTHER PUBLICATIONS

SIPO, Notification of the First Office Action, Chinese Patent Application No. 2015800110305 (foreign counterpart application to U.S. Appl. No. 15/121,830), dated Feb. 26, 2018. (with English translation).

*Primary Examiner* — Blake A Tankersley
(74) *Attorney, Agent, or Firm* — Renner, Kenner, Greive, Bobak, Taylor & Weber

(57) ABSTRACT

An apparatus for carrying out bi-directional load testing of close ended driven piles and injection piles utilizing a hydraulic jack, comprising an enclosure for housing the hydraulic jack (13). The enclosure (1) includes a first hollow body (10) a second hollow body (15). The first hollow body (10) had a covered upper end (10a) and an open lower end (10b), with the upper end being capped by an attached top plate (11) having an external surface (11a) which the lower end (81b) of a first pile (81) may be axially attached to, and an internal surface (11b). The open lower end (10b) has a cut-out (12) originating on the edge of the open end (10b) of the first hollow body for receiving a hydraulic connection (14) for the jack (13). The second hollow body (15) is capable of housing the hydraulic jack (13), has an open upper end (15a) and a lower end (15b). The lower end (15b) is capped by an attached base plate (17) having an external
(Continued)

surface (17a) which the upper end (82a) of a second pile (82) may be axially attached to, and an internal surface (17b) for attaching the base (13a) of the hydraulic jack, and an opening (16) on the capped lower end (15b) originating at a point where the edge of the lower end (15b) abuts the base plate (17) for receiving the hydraulic connection (14) for the jack. The first hollow body (10) and the second hollow body (15) are capable of axial movement relative to one another when actuated by the hydraulic jack.

11 Claims, 10 Drawing Sheets

(51) Int. Cl.
    *G01N 3/10*     (2006.01)
    *E02D 7/02*     (2006.01)

(52) U.S. Cl.
    CPC .......... *E02D 2200/165* (2013.01); *E02D 2200/1628* (2013.01); *E02D 2200/1678* (2013.01); *E02D 2200/1685* (2013.01); *E02D 2600/10* (2013.01); *E02D 2600/20* (2013.01); *G01N 2203/0042* (2013.01)

(56) References Cited

U.S. PATENT DOCUMENTS

| | | | |
|---|---|---|---|
| 2006/0021446 A1* | 2/2006 | England | E02D 33/00 |
| | | | 73/784 |
| 2006/0213279 A1 | 9/2006 | Choi et al. | |
| 2011/0283816 A1* | 11/2011 | Hayes | E02D 33/00 |
| | | | 73/862.627 |

* cited by examiner

APPARATUS FOR BI-DIRECTIONAL LOAD TESTING OF DRIVEN PILES AND INJECTION PILES, AND METHOD THEREOF

FIELD OF THE INVENTION

The present invention relates to the field of geotechnical engineering and deep foundations, specifically the load testing of driven piles and injection piles to verify the load bearing capacity and performance of a pile.

BACKGROUND

Piles are used to prepare the foundation of a structure such as a building, and the depth and load bearing capacity of a pile are critical factors which must be considered and verified when carrying out deep foundation works.

Driven piles and injection piles are both pre-fabricated piles which are usually made of steel, reinforced concrete, wood or a composite of steel and concrete, and differ only in the method which is used to embed the pile into the ground.

A driven pile as the name suggests, is a pile which is driven into the ground mechanically with a pile-driver.

Similarly, an injection pile is a pile which is injected or jacked into the ground mechanically, using a high-capacity hydraulic jacking machine.

Driven piles and injection piles comprise of both the close-ended and the open-ended variety. A close ended driven pile would generally be a steel pipe with a cast steel shoe covering the bottom of the pile, a steel H-beam, or a square or triangular pile with a covered end. An open ended pile, may generally be a steel pipe or tube with an open bottom end, which permits earth to enter the pipe as the pile is driven into the ground.

The verification of the load bearing capacity and the integrity of a pile depends on a number of factors such as ground conditions, availability of test pile data for specific ground conditions and/or specific piling techniques, and involves carrying out both preliminary and/or working pile tests.

For example, the Federation of Piling Specialists Handbook on Pile Load Testing specifies that piling works being carried out on complex or unknown ground conditions, with no previous pile test data available and/or using a new piling technique constitutes a high level of risk, making both preliminary and working pile tests essential, at a rate of one preliminary pile test for every 250 piles, and one working pile test for every 100 piles.

There are a number of load testing methods currently in use, such as the reaction pile method, the kentledge method and the bi-directional load cell method, which all fall under the category of Maintained Load Tests.

Traditionally, the kentledge method is most commonly used for the load testing of driven piles and injection piles. The kentledge method involves equipping a test pile with instrumentation such as dial gauges and load cells to measure displacement, and placing a discrete and incremental load up to a maximum of 120% of the test load on a test frame assembled over a test pile for an extended period of time, and then monitoring and taking measurements of the resulting pile movement and settlement.

However, the kentledge method has a number of drawbacks. The primary one being the test load used in the kentledge method which is generally in the form of concrete blocks or steel ingots of regular dimensions and weight. These concrete blocks are trucked-in to a work-site and then lifted with a crane and stacked incrementally on the test frame. Due to the sheer weight and bulk of the concrete blocks and the rising cost of fuel and transportation, the kentledge method has become increasing expensive and less cost effective. This is particularly true for test loads in the 300 ton range, where the transportation costs increases exponentially for test loads above 300 tons.

Other drawbacks of the kentledge method are:
the requirement for a large working area due to the need for a crane and sufficient area for the delivery and storage of the concrete blocks, and
the inherent risk of collapse of the test frame on complex or unknown ground conditions which poses a danger to workers manning and monitoring the test instrumentation.

Although there are other Maintained Load Test methods mentioned above such as the bi-directional load test cell which is safer, this method is only applicable for load testing of augered or bored piles, and is not suited for testing of driven piles.

The bi-directional load test method involves placing one or more load cell containing a hydraulic jack either at the pile base, or part way up the bored pile shaft, and then expanding the test cell hydraulically so that the upper part of a bored pile reacts against the lower part of the pile. However, there exists no apparatus to apply the bi-directional load test method to driven piles.

With the drawbacks of the kentledge method in mind, it is desirable to have a test method and apparatus to facilitate the load testing of driven piles which is more economical, and which is safer to operate.

In view of the absence of a comparable bi-directional load test system for driven piles, it is further desirable to provide an apparatus which allows such a load testing method to be applied to driven piles.

The present invention was developed in consideration of the above requirements.

SUMMARY OF THE INVENTION

In a first embodiment of the invention, an apparatus for carrying out bi-directional load testing of driven piles and injection piles specifically the close ended variety utilizing a hydraulic jack, which comprises an enclosure for housing a hydraulic jack is disclosed.

The enclosure for housing the hydraulic jack includes a first hollow body and a second hollow body.

The first hollow body has an upper end and an open lower end. The upper end is capped by an attached top plate having an external surface which the lower end of a first driven pile may be axially attached to, and also an internal surface. The first hollow body also has a cut-out originating on the edge of its open end for receiving a hydraulic connection for the jack.

The second hollow body is capable of housing the hydraulic jack, and has an open upper end and a lower end. The lower end is capped by an attached base plate having an external surface which the upper end of a second driven pile may be axially attached to and an internal surface for attaching the base of the hydraulic jack. The second hollow body also has an opening for receiving the hydraulic connection for the jack on the capped lower end which originates at a point where the edge of the lower end abuts the base plate.

The first hollow body is capable of axial movement relative to the second hollow body when actuated by the hydraulic jack, such that in one variant of the first embodiment, the first hollow body axially receives the second hollow body through the open lower end of the first hollow body, while in another variant of the first embodiment, the first hollow body is axially received by the second hollow body through the open upper end of the second hollow body.

The hydraulic jack utilized in the first embodiment of the invention is typically a capsule jack, which due to its physical shape, is most suited for use in the apparatus.

In another variant of the first embodiment of the invention, a shield is attached to and extends perpendicularly from an edge of the upper surface of the base plate of the second hollow body at a position which corresponds to the opening on the second hollow body.

In still another variant of the first embodiment, the shield comprises a housing which has an open upper end, and a wedge-shaped lower end.

In a further variant of the first embodiment, the second hollow body may additionally house a load cell which is stacked on top of the hydraulic jack.

In a further variant of the first embodiment, an extensor meter may be attached between the top plate of the first hollow body, and the base plate of the second hollow body.

The apparatus according to the first embodiment of the invention may be adapted for the bi-directional load testing of cylindrical or pipe piles, square piles or H-piles, and triangular piles.

For cylindrical or pipe piles, the apparatus according to the first embodiment of the invention would have an enclosure that is cylindrical, octagonal or even hexagonal in cross-section.

For square piles or H-piles, the enclosure would accordingly have a square cross-section.

In the case of triangular piles, the enclosure would accordingly have a triangular cross-section.

A method for carrying out bi-directional load testing of close ended driven piles and injection piles using the apparatus according to the first embodiment of the invention is also disclosed.

The method comprises the following steps:
a) attaching the lower end of a first close ended driven pile or injection pile to the external surface of the top plate of the first hollow body,
b) attaching the upper end of a second close ended driven pile or injection pile to the external surface of the base plate of the second body,
c) connecting hydraulic line to the hydraulic connection and pressure testing the hydraulic jack housed in the apparatus,
d) driving the first driven pile or injection pile, the apparatus and the second driven pile or injection pile into the ground, and
e) pressurizing the hydraulic jack to simulate the loads to be tested, and obtaining the corresponding load test data.

The method for carrying out bi-directional load testing of close ended driven piles and injection piles using the apparatus according to the first embodiment of the invention, may also be utilized for the load testing of longer piles which comprises more than two piles which are spliced together. In such a case, the apparatus according to the first embodiment of the present invention is attached between pairs of spliced piles to obtain load test data from individual splice positions along the longer pile.

In a second embodiment of the invention, an apparatus for carrying out bi-directional load testing of open ended driven piles and injection piles utilizing a hydraulic jack, comprising a first cylindrical shaped hollow body, a second cylindrical shaped hollow body and a third cylindrical shaped hollow body is disclosed.

The first cylindrical shaped hollow body has an open upper end, an open lower end and an opening on its side wall for receiving a hydraulic connection.

The first hollow body also has a means for securing a hydraulic jack which comprises a first hub member having an upward apex and a base for attaching the top of a hydraulic jack, and a plurality of fin members.

Each of the plurality of fin members has an outer edge which is parallel to the axis of the first hollow body, a top edge which is parallel to the upper end of the first hollow body and having a length corresponding to the inner radius of the first hollow body, an inner edge corresponding to the apex of the first hub member, and a bottom edge which is parallel to the base of the first hub member.

When the first hollow body is in assembled form, the plurality of fin members are attached to the inner wall of the first hollow body, extends radially from the inner wall of the first hollow body and converges at the axis of the first hollow body.

The second cylindrical shaped hollow body has an open upper end and an open lower end, and further comprises a second hub member having a downward apex and a base for attaching the base of a hydraulic jack, and a plurality of fin members.

Each of the plurality of fin members has an outer edge which is parallel to the axis of the second hollow body, a bottom edge which is parallel to the lower end of the second hollow body, a length which corresponds to the inner radius of the second hollow body, an inner edge which corresponds to the apex of the second hub member, and a top edge which is parallel to the bottom edge of the second hollow body.

When the second hollow body is in assembled form, the plurality of fin members are attached to the inner wall of the second hollow body, extends radially from the inner wall of the second hollow body and converges at the axis of the second hollow body.

The inner and outer diameters of the first hollow body and the second hollow body respectively correspond to one another.

The third cylindrical shaped hollow body has an open upper end and an open lower end. The third hollow body also has an inner diameter corresponding to the outer diameter of the first hollow body and the second hollow body, and is capable of being axially received by both the first hollow body and the second hollow body.

When the apparatus is in the assembled state, the upper end of the second hollow body abuts against the lower end of the first hollow body, the third hollow body is received by both the first and second hollow bodies, and the lower end of the third hollow body abuts the top edge of the plurality of fin members of the second hollow body.

In one variant of the second embodiment, a shield is attached to the surface of the first hollow body at a position corresponding to the opening on the first hollow body.

In another variant of the second embodiment, the first and second hub members are cone shaped.

In a further variant of the second embodiment, the first and second hub members are pyramid shaped.

A method for carrying out bi-directional load testing of open ended driven piles and injection piles using the apparatus according to the second embodiment of the invention is also disclosed.

The said method comprises the following steps:
a) attaching the lower end of a first open ended driven pile or injection pile to the upper end of the first hollow body,
b) attaching the upper end of a second open ended driven pile or injection pile to the lower end of the second body,
c) connecting hydraulic line to the hydraulic connection and pressure testing the hydraulic jack housed in the apparatus,
d) driving the first driven pile or injection pile, the apparatus and the second driven pile or injection pile into the ground, and
e) pressurizing the hydraulic jack to simulate the loads to be tested, and obtaining the corresponding load test data.

The method for carrying out bi-directional load testing of open ended driven piles and injection piles using the apparatus according to the second embodiment of the present invention, may also be utilized for the load testing of longer piles comprising more than two piles which have been spliced together. In such a case, the apparatus according to the second embodiment of the present invention is attached between pairs of spliced piles to obtain load test data from individual splice positions along the longer pile.

BRIEF DESCRIPTION OF THE DRAWINGS

The invention is illustrated, though not limited by the following description of embodiments that are being given by way of example only, with reference to the accompanying drawings in which.

DETAILED DESCRIPTION AND BEST MODE

Figure 1:
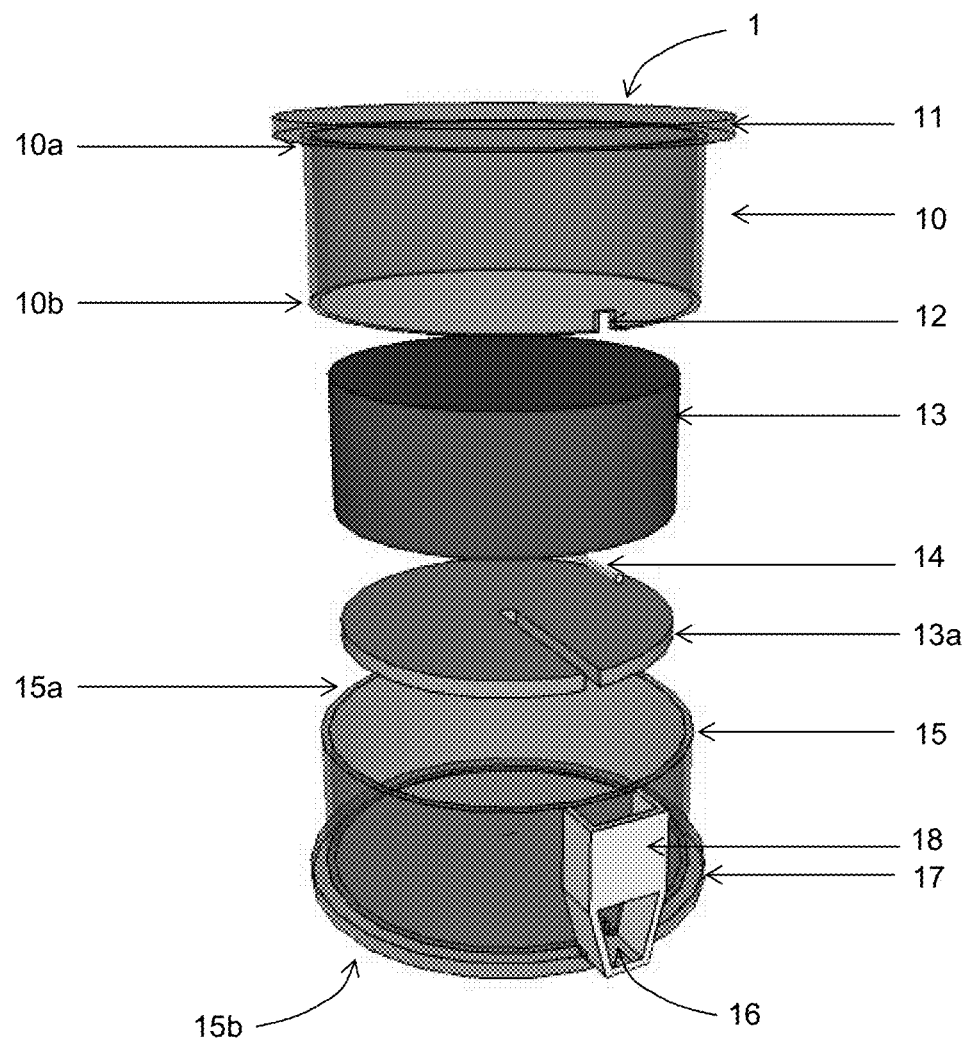
FIG. 1 illustrates a first perspective view of the first embodiment of the invention.
Figure 2:
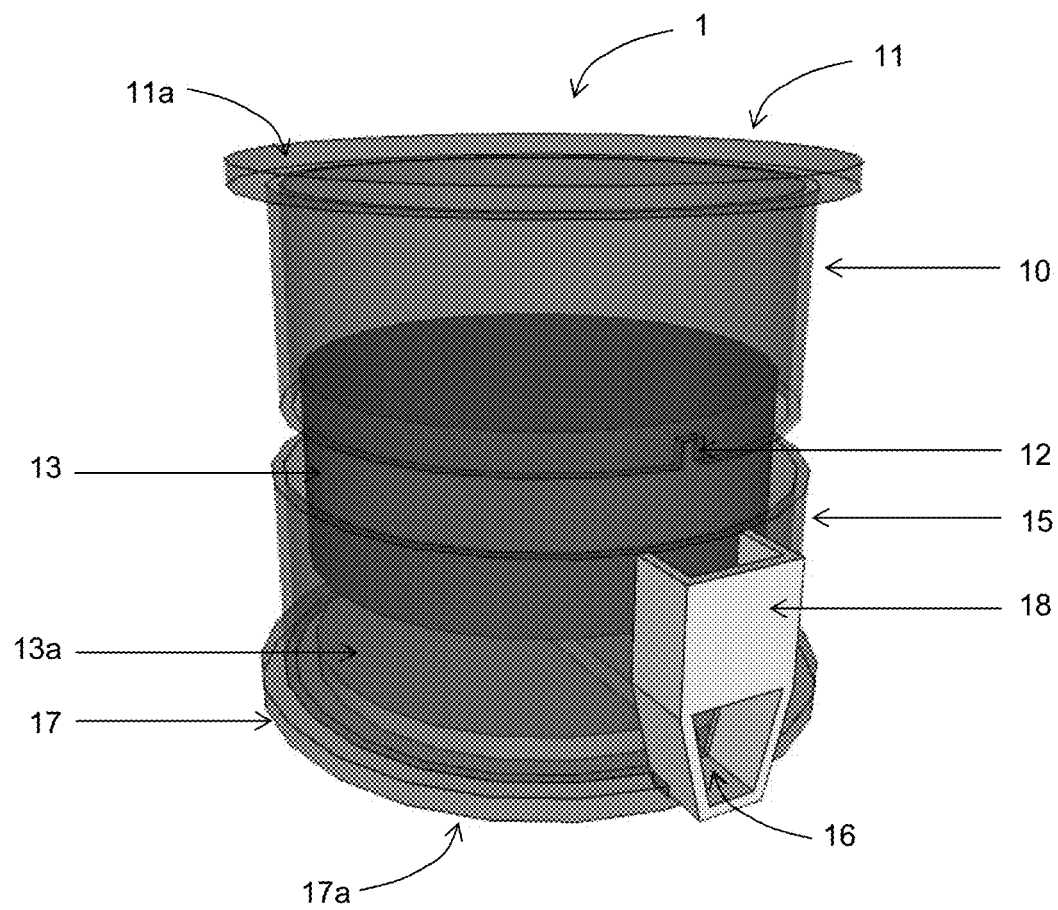
FIG. 2 illustrates a second perspective view of the first embodiment of the invention.
Figure 3:
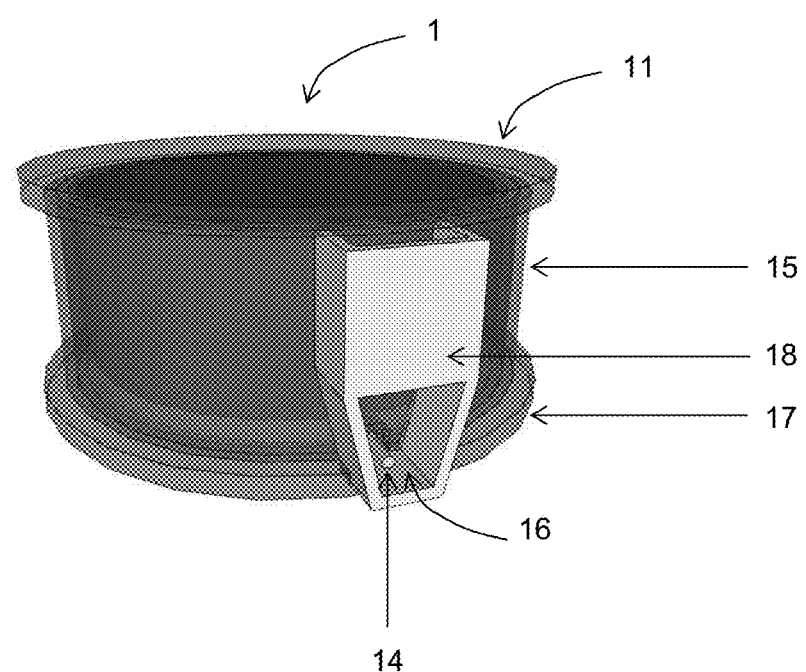
FIG. 3 illustrates a third perspective view of the first embodiment of the invention.

FIGS. 1 to 3 illustrate in perspective view, the first embodiment of the invention, specifically an apparatus for carrying out bi-directional load testing of close ended driven piles and injection piles utilizing a hydraulic jack.

FIG. 1 is specifically an exploded perspective view of the apparatus, and illustrates the individual components which the apparatus comprises of, while FIGS. 2 and 3 illustrates in perspective view, how the individual components are assembled and positioned relative to one another.

The apparatus according to the first embodiment of the invention comprises an enclosure 1 for housing a hydraulic jack 13 which includes a first hollow body 10 and a second hollow body 16.

The first hollow body 10 has an upper end 10a which is capped by a top plate 11, an open lower end 10b and a cut-out 12 originating at the lower end of the first hollow body.

The top plate 11 has both an external surface 11a which the lower end of a first close ended driven pile or injection pile is attached to, and an internal surface 11b.

The cut-out 12 on the lower end is to receive the hydraulic connection 14 of the hydraulic jack 13.

The second hollow body 15 which houses the hydraulic jack 13, has an open upper end 15a, a lower end 15b capped by a base plate 17, and an opening 16 for receiving the hydraulic connection 14 of the hydraulic jack on the capped lower end 15b, which originates at a point where the lower end abuts the base plate 17.

The base plate 17 has an external surface 17a and an internal surface 17b. The hydraulic jack is attached to the internal surface 18b of the second hollow body via its base 13a. The upper end of a second close ended pile under test is attached to the external surface 17a of the base plate.

The hydraulic jack 13 housed in the second hollow body is preferably a capsule jack. A capsule jack is so named as it essentially comprises a capsule shaped shell housing an expandable bladder which pushes against a piston when pressurized with hydraulic fluid, and is particularly suited for the apparatus by virtue of its shape and compact dimensions, although the invention is not limited to its use solely. The capacity of the hydraulic jack to be housed in the enclosure is dependent on the maximum load that is to be borne by the pile.

FIGS. 1 to 3 also illustrate a shield 18 which is attached to the base plate 17 of the second hollow body. The shield is attached to and extends perpendicularly from an edge of the rim of the base plate at a position which corresponds to the opening on the second hollow body. The shield serves to protect the hydraulic connection when the pile under test is being driven or injected into the ground, while still allowing access to the hydraulic connection, for a hydraulic line or hose to be connected to the hydraulic jack and then tightened using an appropriate tool, such as a wrench or a spanner.

Although not shown in the drawings, the hydraulic line or hose 19 is typically fed through a protective sleeve or duct which is axially attached to a pile under test. The shield also serves to protect the hydraulic line or hose at the point where the protective sleeve or duct originates.

The shield 18 as illustrated in FIGS. 1 to 3, comprises a housing which has a wedged shaped lower end to aid in displacing the surrounding earth when the pile under test is driven or injected into the ground, and an open upper end that allows access by the hydraulic line or hose and its protective sleeve or duct.

The first hollow body 10 and the second hollow body 15 are capable of axial movement relative to one another. In order to facilitate the relative axial movement, the open lower end of the first hollow body corresponds to the open upper end of the second hollow body.

In the first embodiment of the invention, the first hollow body 10 is received by the second hollow body 15, through the open upper end 15*a* of the second hollow body. This is in other words means that the first hollow body is also housed by the second hollow body as illustrated in FIGS. 2 and 3. Accordingly, the shape of the first hollow body must match that of the second hollow body, and the external physical dimensions of the first hollow body, e.g., its circumference, must at least be smaller than of the internal physical dimensions of the second hollow body.

Figure 4:
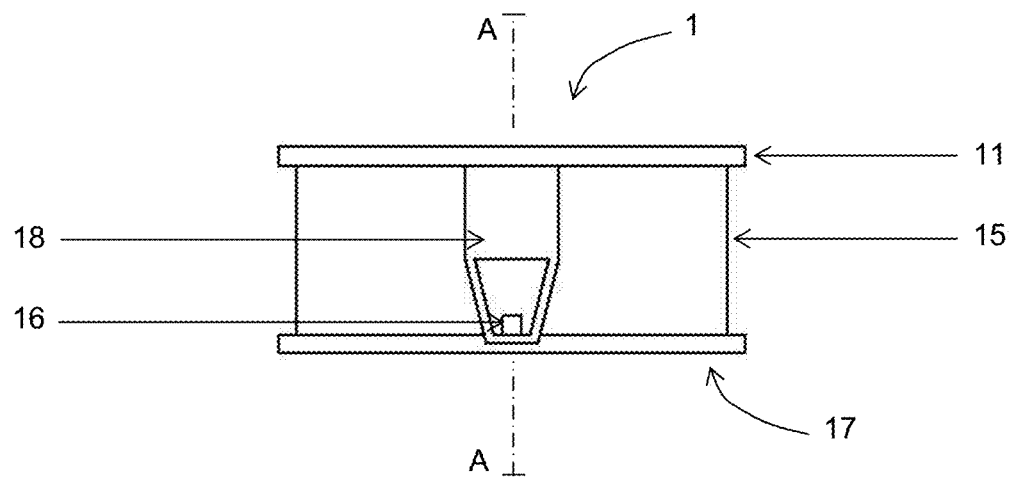
FIG. 4 illustrates a first frontal view of the first embodiment of the invention.
Figure 5:
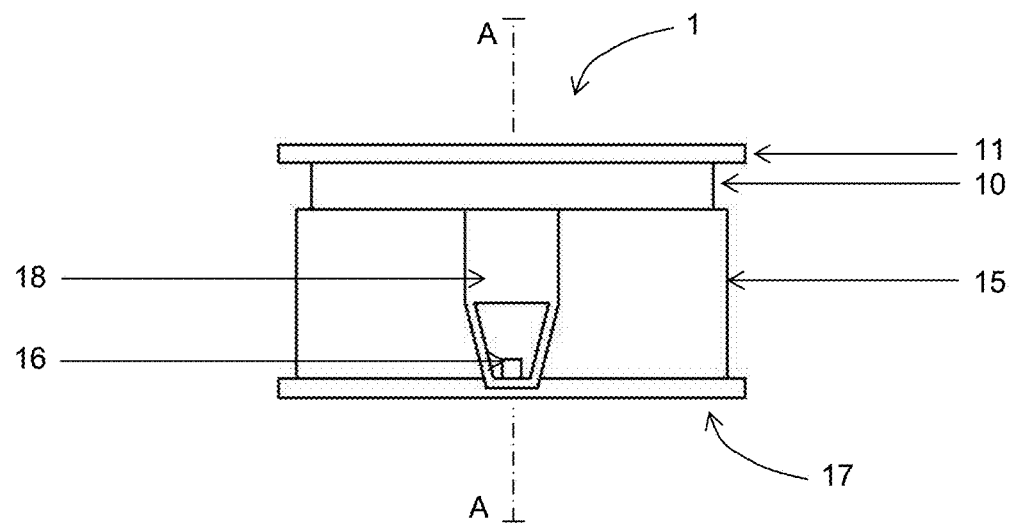
FIG. 5 illustrates a second frontal view of the first embodiment of the invention.
Figure 6:
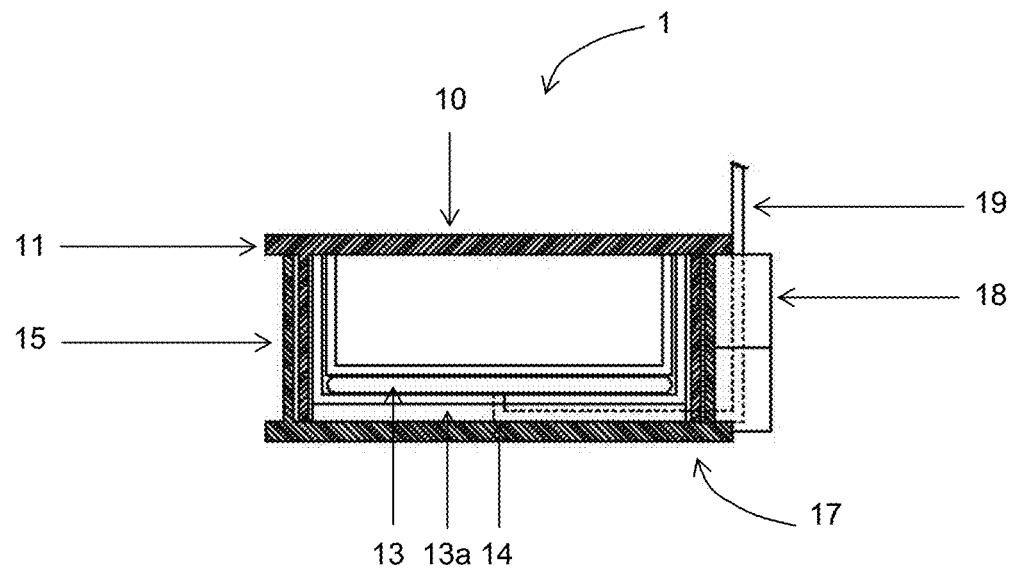
FIG. 6 illustrates a first cross-sectional view of the first embodiment of the invention taken along line A-A of FIG. 4.
Figure 7:
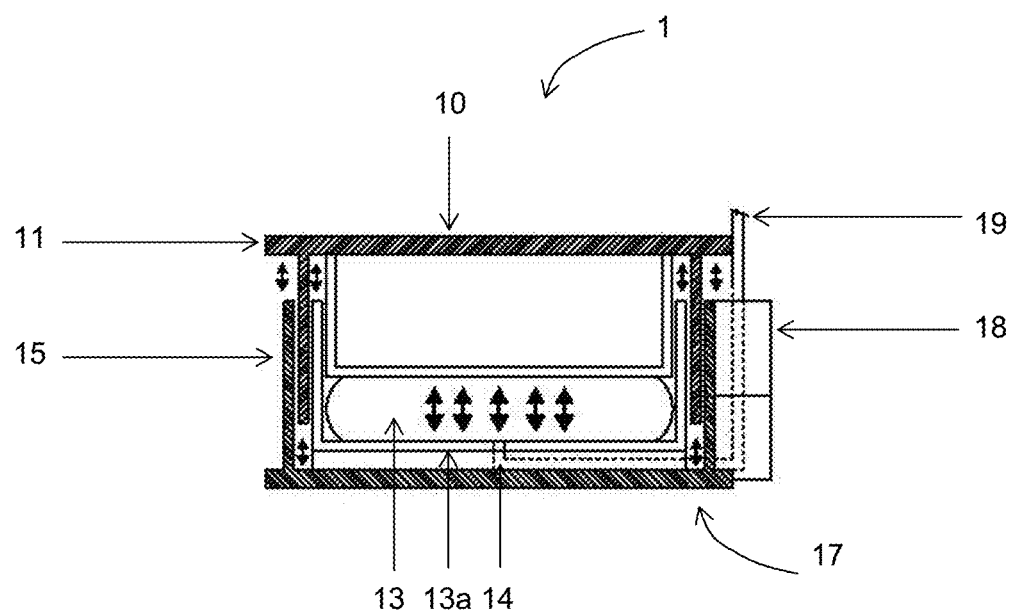
FIG. 7 illustrates a second cross-sectional view of the first embodiment of the invention taken along line A-A of FIG. 5.

The apparatus according to the first embodiment of the invention illustrated in FIGS. 1 to 3, is further illustrated in the front view in FIGS. 4 and 5, and in the cross-sectional view (taken along line A-A) in FIGS. 6 and 7.

FIGS. 4 and 6 illustrate the apparatus when it is in the rest or idle position, i.e. when the hydraulic jack 13 has not been actuated.

In the rest or idle position, the first hollow body 10 is received by the second hollow body 15 and rests within the second hollow body, with the edge of the top plate of the first hollow body resting on the edge of the open upper end of the second hollow body.

FIGS. 5 and 7 illustrate the apparatus when it is in use, i.e., when the hydraulic jack 13 is actuated.

When the hydraulic jack 13 is actuated, the first hollow body 10 is pushed by the hydraulic jack and will move axially upward relative to the second hollow body 15. The first hollow body will in other words move away or apart from the second hollow body which the first hollow body is received into.

The apparatus according to the first embodiment of the invention is not limited to the variant described above. In another variant of the first embodiment, the first hollow body 10 instead receives the second hollow body 15, through the open lower end 10*b* of the first hollow body. In other words, the second hollow body is housed by the first hollow body. Accordingly, the shape of the second hollow body must match that of the first hollow body, and the external physical dimensions of the second hollow body, e.g., its circumference, must at least be smaller than of the internal physical dimensions of the first hollow body.

The enclosure 1 for housing the hydraulic jack according to the first embodiment of the invention, is typically constructed sheet metal, and may comprise steel pipe sections, or even steel plates cut and welded to fabricate an enclosure with a cross-section of a specific shape.

Although FIGS. 1 to 7 illustrate the first embodiment of the invention with the enclosure 1 as having a cylindrical shaped cross-section, this has been done solely for exemplary purposes.

The apparatus according to the first embodiment of the invention is not limited to an enclosure 1 having a cylindrical cross section. An enclosure having cylindrical shaped cross section is generally intended for cylindrical piles or pipe piles. The enclosure 1 may also have a hexagonal or octagonal cross section, which may be used in case a cylindrical cross section of a specific dimension is not readily available.

Similarly, the enclosure 1 may have a cross section which is square shaped if the apparatus is to be used with square piles or H-piles, and a cross section which is triangular shaped if the apparatus is to be used with a triangular pile.

The enclosure 1 of the apparatus according to the first embodiment of the invention may optionally and additionally house a load cell if there is a requirement for one. Although not shown in the drawings, a load cell may be stacked on top of the hydraulic jack housed in the second hollow body, and the hydraulic line of the load cell would accordingly be received by the opening on the second hollow body, and also routed through the protective sleeve or duct.

The apparatus according to the first embodiment of the invention may also incorporate an extensor meter which would typically have one end attached between the top plate of the first hollow body, and the other end attached to the base plate of the second hollow body. The control lines would also be routed through the protective sleeve or duct.

In the field of geotechnical engineering and deep foundations, it is established practice for one or more tell-tale lines to be connected to the apparatus to provide a visual indication of the axial movement or displacement of the first hollow body relative to the second hollow body. The incorporation of a load cell and an extensor meter as described above serves to provide an instrumented means of monitoring and measuring precisely the displacement or axial movement of the first hollow body relative to the second hollow body during the course of load testing, in addition to the well known use of the tell-tale lines.

Driven piles and injection piles are generally available in specific lengths, and a single pile would not be of sufficient length for foundations requiring a greater depth. In order to obtain a pile capable of being embedded in the ground to a greater depth, a second pile may be spliced to the end of a first pile, to form a pile with a greater length.

Depending on the depth required for a foundation, an additional third pile may be spliced to the end of the second pile and a fourth pile may in turn be spliced to the end of the third pile. This is widely practiced in the field of geotechnical engineering and deep foundation works.

Figure 8:
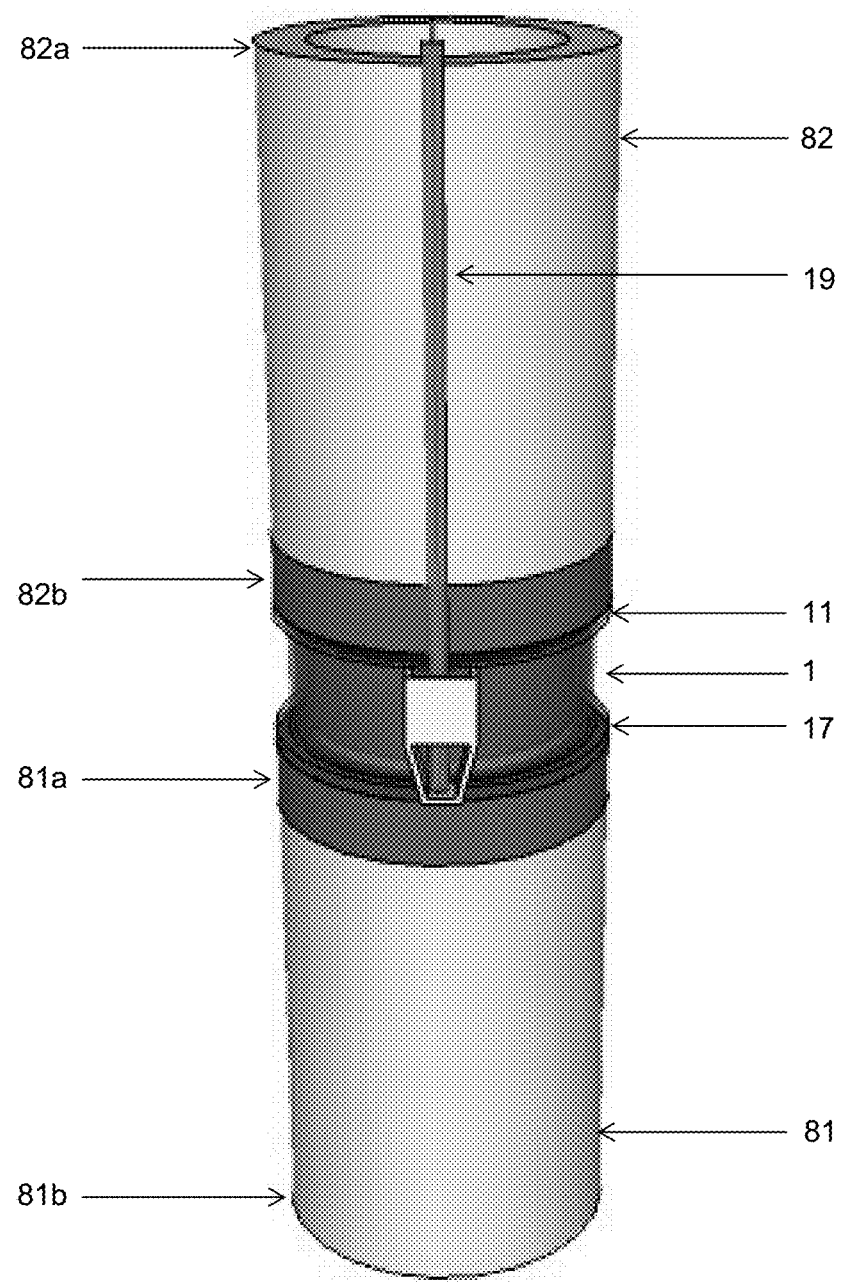
FIG. 8 illustrates in the perspective view, the first embodiment of the invention in use, with a first pile and a second pile attached.

FIG. 8 illustrates how the bi-directional load testing of close ended driven piles or close ended injection piles which have been spliced together is accomplished by attaching a unit of the apparatus according to the first embodiment of the invention between a first pile 81 and a second pile 82 which are to be combined to form a pile of greater length. The method involves the following steps:

a) Attaching the upper end 81*a* of a first close ended driven pile or injection pile to the external surface 17*a* of the base plate 17 of the second hollow body 15 by welding or other mechanical means.

b) Attaching the lower end 82*b* of a second close ended driven pile or injection pile to the external surface 11*a* of the top plate 11 of the first hollow body 10 by welding or other mechanical means.

c) Connecting a hydraulic line or hose to the hydraulic connection 14 of the hydraulic jack 13 housed in the enclosure 1 of the apparatus, and then pressure testing the hydraulic jack to ensure it is functioning.

d) Embedding the first driven pile or injection pile, the apparatus and the second driven pile or injection pile into the ground.

e) Pressurizing the hydraulic jack 13 to simulate the loads to be tested, and obtaining the corresponding load test data.

Steps a) and b) are interchangeable, and may be dictated by the user's practice or requirements.

The method may alternatively include the additional step of embedding the lower end (81*b*) of the first close ended driven pile or injection pile into the ground, before carrying out step a).

At step c), if the pressure testing indicates or detects a hydraulic failure or leak in the hydraulic jack, the defective apparatus is detached and replaced, and the replacement apparatus is then subject to the same pressure testing.

The method for carrying out bi-directional load testing of close ended driven piles and injection piles described above may also be used in cases where more than two piles are spliced together to form a longer pile. In such cases, a unit of the apparatus is attached between pairs of spliced piles if load test data from individual splice positions along the longer pile are required.

The apparatus according to the first embodiment of the invention is sufficiently versatile to allow modification to the method described above, and still be capable of carrying out bi-directional load testing.

In a variant of the method for carrying out bi-directional load testing of close ended driven piles and injection piles, step a) may be modified so that the upper end 81*a* of a first close ended driven pile or injection pile is instead attached to the external surface 11*a* of the top plate 11 of the first hollow body 10, and step b) may be modified so that the lower end 82*b* of a second close ended driven pile or injection pile is instead attached to the external surface 17*a* of the base plate 17 of the second hollow body 15.

In a further variant of the method for carrying out bi-directional load testing of close ended driven piles and injection piles, the apparatus according to the first embodiment of the invention may also be used for the load testing of a close ended driven pile or injection pile which is used as an end bearing pile. The method includes the steps of:
a) Attaching the lower end of a close ended driven pile or injection pile to the external surface 17*a* of the base plate 17 of the second hollow body 15 by welding or other mechanical means.
b) Connecting a hydraulic line or hose to the hydraulic connection 14 of the hydraulic jack 13 housed in the enclosure 1 of the apparatus, and then pressure testing the hydraulic jack to ensure it is functioning.
c) Embedding fully the driven pile or injection pile and the apparatus into the ground.
d) Pressurizing the hydraulic jack 13 to simulate the loads to be tested, and obtaining the corresponding load test data.

Figure 9:
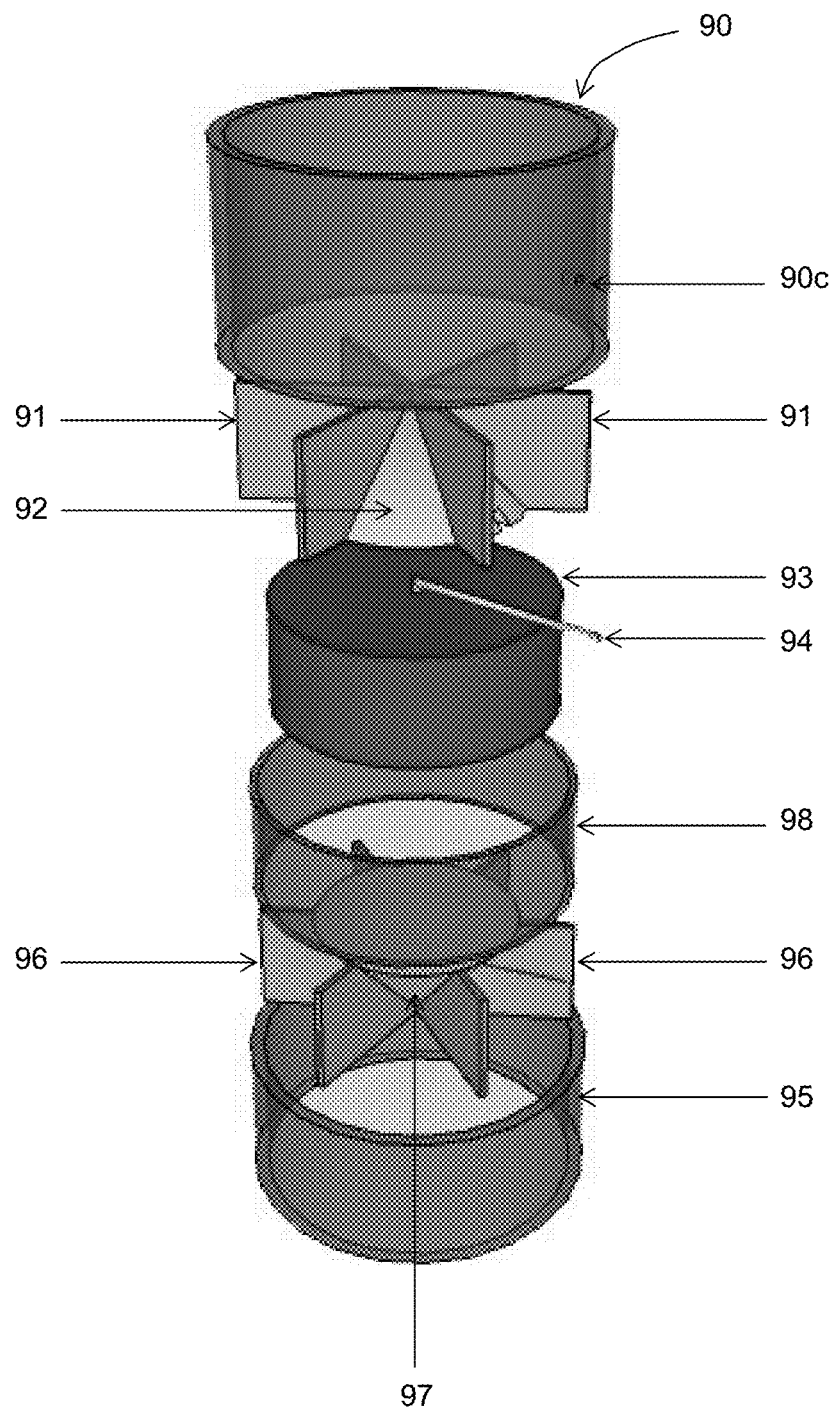
FIG. 9 illustrates a first perspective view of the second embodiment of the invention.
Figure 10:
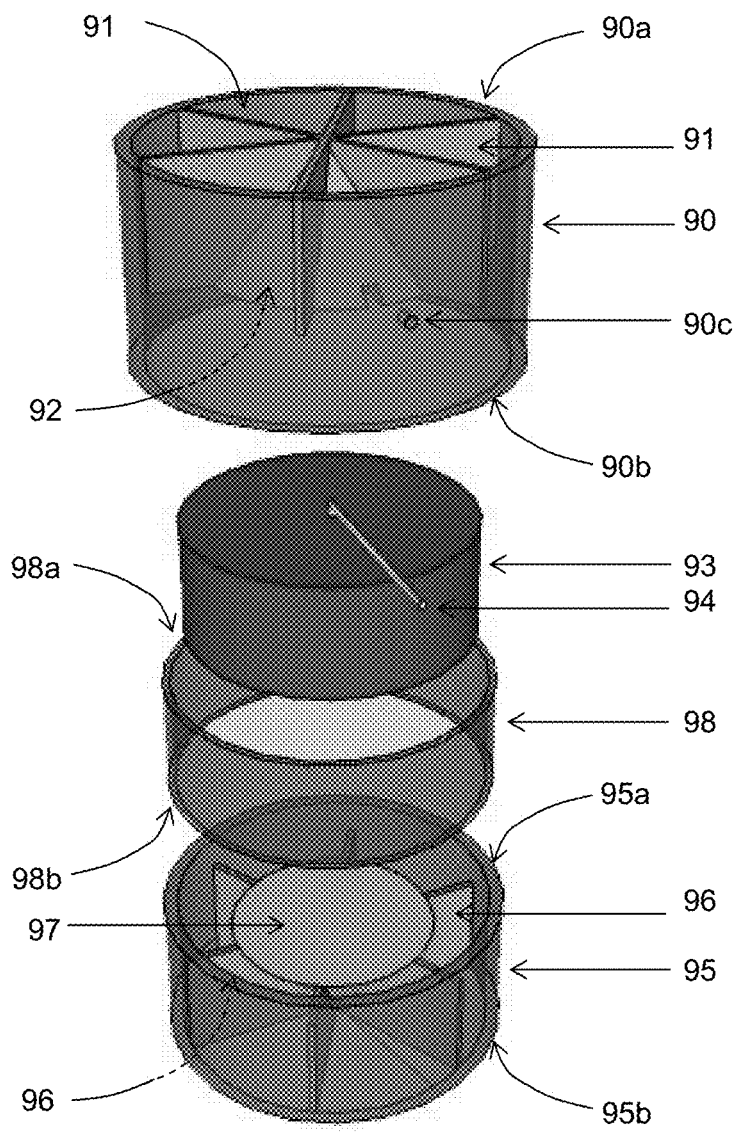
FIG. 10 illustrates a second perspective view of the second embodiment of the invention.
Figure 11:
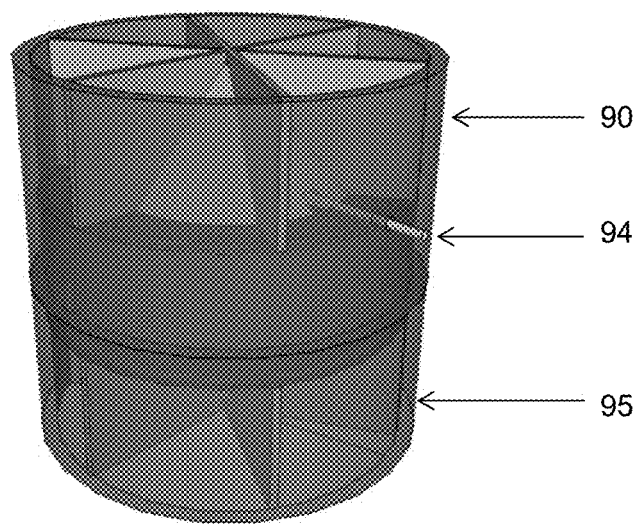
FIG. 11 illustrates a third perspective view of the second embodiment of the invention.
Figure 12:
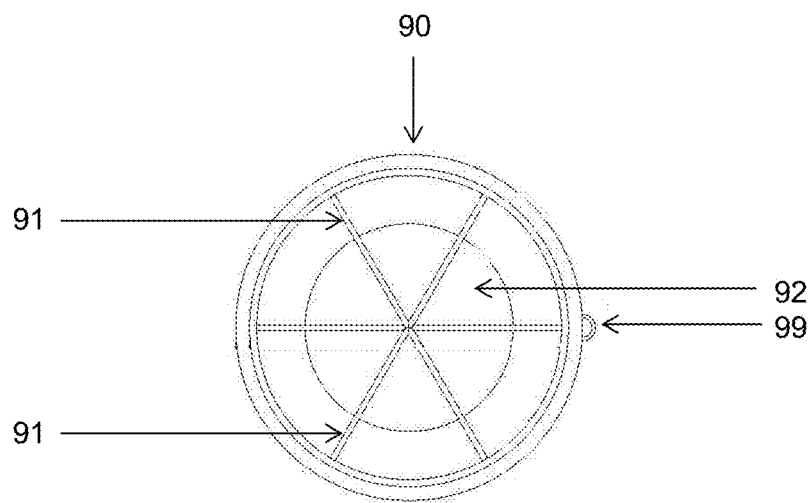
FIG. 12 illustrates a top view of the second embodiment of the invention.

FIGS. 9 to 11 illustrate in perspective view, the second embodiment of the invention, specifically an apparatus for carrying out bi-directional load testing of open ended driven piles and injection piles utilizing a hydraulic jack. FIG. 12, in turn illustrates the apparatus according to the second embodiment of the invention in the top view.

FIG. 9 is specifically an exploded perspective view of the apparatus, and illustrates the individual components which the apparatus comprises of, while FIGS. 9 and 10 illustrates in perspective view, how the individual components are assembled and positioned relative to one another.

The apparatus according to the second embodiment of the invention comprises a first cylindrical shaped hollow body 90, a second cylindrical shaped hollow body 95 and a third cylindrical shaped hollow body 98, for housing a hydraulic jack 93.

The first cylindrical shaped hollow body 90 has an open upper end 90*a*, an open lower end 80*b* and an opening 90*c* on its side wall 90*c* for receiving a hydraulic connection 94. The open upper end and the open lower end allow for the movement of the surrounding earth or soil into the open ended pile when the pile is being driven or injected into the ground.

The first hollow body 90 also has a means for securing a hydraulic jack 93 which comprises a first hub member 92 that has an upward apex 92*a* and a base 92*b* for attaching the top of a hydraulic jack, and a plurality of fin members 91 for supporting the first hub member.

Each of the plurality of fin members 91 has the following features:
an outer edge which is parallel to the axis of the first hollow body,
a top edge which is parallel to the upper end of the first hollow body and having a length corresponding to the inner radius of the first hollow body,
an inner edge corresponding to the apex of the first hub member, and
a bottom edge which is parallel to the base of the first hub member.

From FIG. 12, it can be seen that in assembled form, the plurality of fin members 91 are attached to the inner wall of the first hollow body 90, extend radially from the inner wall of the first hollow body and converge at the axis of the first hollow body.

The first hollow body 90, the plurality of fin members 91 and the first hub member 92 are typically fabricated from steel plate. The outer edge of each fin member is attached to the inner wall of the first hollow body by welding each outer edge to the surface of the inner wall, and the inner edge of each fin member is attached to the first hub member by welding the inner edge to the surface of the first hub member.

The purpose of the upward apex of the first hub member 92 and the plurality of fin members is to aid and prevent obstruction of the movement of earth or soil surrounding the open ended pile.

The second cylindrical shaped hollow body 95 has an open upper end 95*a* and an open lower end 95*b*, and further comprises a second hub member 97 having a downward apex 97*a* and a base 97*b* for attaching the base of a hydraulic jack 93, and a plurality of fin members 96 for supporting the second hub member.

Each of the plurality of fin members 96 has the following features:
an outer edge which is parallel to the axis of the second hollow body,
a bottom edge which is parallel to the lower end of the second hollow body and having a length corresponding to the inner radius of the second hollow body,
an inner edge corresponding to the apex of the second hub member, and
a top edge which is parallel to the bottom edge of the second hollow body.

In the assembled form, the plurality of fin members 96 are attached to the inner wall of the second hollow body 95, extend radially from the inner wall of the second hollow body and converge at the axis of the second hollow body.

The second hollow body 95, the plurality of fin members 96 and the second hub member 97 are also typically fabricated from steel plate. The outer edge of each fin member is attached to the inner wall of the second hollow body by welding each outer edge to the surface of the inner wall, and the inner edge of each fin member is attached to the second hub member by welding the inner edge to the surface of the second hub member.

The purpose of the downward apex of the second hub member 97 and the plurality of fin members is similarly to aid and prevent obstruction of the movement of earth or soil surrounding the open ended pile, in a similar fashion as the first hollow body.

The inner and outer diameters of the first hollow body and the second hollow body respectively correspond to one another, and both the first hollow body and the second hollow body possess the same internal diameter.

The third cylindrical shaped hollow body 98 has an open upper end 98a and an open lower end 98b. the third hollow body having an inner diameter corresponding to the outer diameter of the first hollow body 90 and the second hollow body 95, and capable of being axially received by both the first hollow body and the second hollow body, When the apparatus according to the second embodiment of the invention is in assembled state, the upper end 95a of the second hollow body 95 abuts against the lower end 90b of the first hollow body 90.

The third cylindrical shaped hollow body 98 is in turn received by both the first and second hollow bodies, and the lower end 98b of the third hollow body abuts the top edge of the plurality of fin members 96 of the second hollow body 95. This arrangement effectively aligns any movement of the first hollow body 90 relative to the second hollow body 95 when the hydraulic jack 93 is actuated.

A hydraulic jack 93 is secured in place by the first hub member 91 and the second hub member 97, and is housed within the first cylindrical shaped hollow body 90 and the second cylindrical hollow body 95. The hydraulic jack 93 is preferably a capsule jack, which is most suited due to its shape and compact dimensions, although the second embodiment is not limited to the sole use of a capsule jack.

Figure 13:
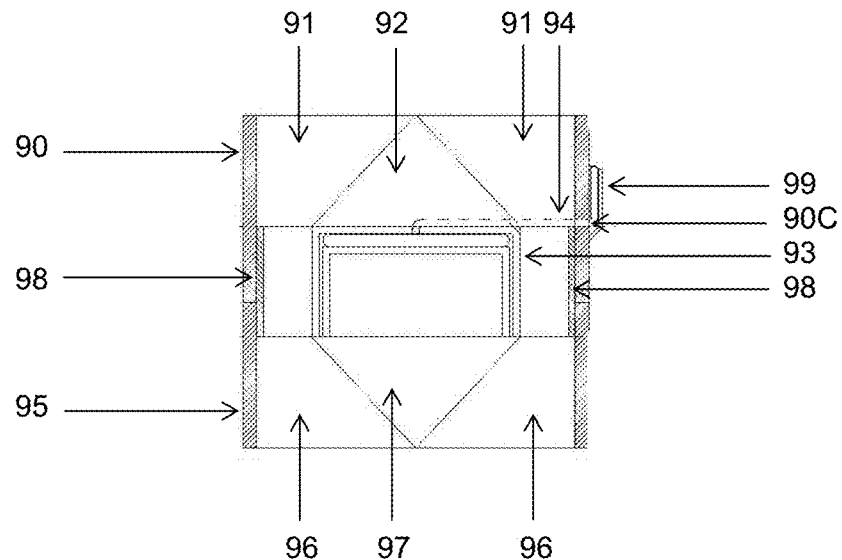
FIG. 13 illustrates a first cross-sectional side view of the second embodiment of the invention.
Figure 14:
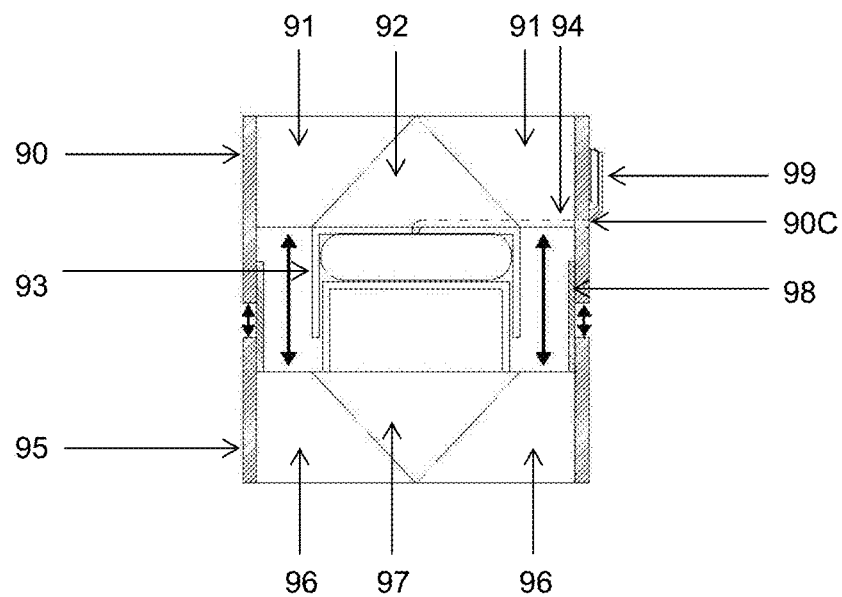
FIG. 14 illustrates a second cross-sectional side view of the second embodiment of the invention.

The apparatus according to the second embodiment of the invention illustrated in FIGS. 9 to 12, is further illustrated in the cross-sectional side view in FIGS. 13 and 14.

Although FIGS. 9 to 14 do not illustrate the apparatus according to a second embodiment of the invention with a shield, one may in fact be attached to the side wall of the first cylindrical shaped hollow body 90 over the opening 90c for the hydraulic connection 94. As explained in the description of the first embodiment, a shield serves to protect the hydraulic connection when the pile under test is being driven or injected into the ground, while providing access to the hydraulic connection.

However, FIGS. 12 to 14 do illustrate a portion of a protective sleeve or duct 99 which is axially attached to the side wall of the first hollow body 90. The protective sleeve or duct 99 originates from the opening 90c on the side wall of the first hollow body, and also protects the hydraulic line or hose of a pile under test. The point where the protective sleeve or duct originates from may in turn be protected by a shield.

FIG. 13 illustrates the apparatus when it is in the rest or idle position, i.e. when the hydraulic jack 93 has not been actuated.

In the rest or idle position, the lower end of the first hollow body 90 rests on, or is abutted by the upper end 95a of the second hollow body 95. The lower end 98b of the third hollow body 98 rests on the upper edge of the plurality of fin members 96 within the second hollow body 95, while the lower edge of the plurality of fin members 91 within the first hollow body 90 rests on the upper end 98a of the third hollow body 98.

FIG. 14 illustrates the apparatus when it is in use, i.e., when the hydraulic jack 93 is actuated.

When the hydraulic jack 93 is actuated, the first hollow body 90 is pushed by the piston of the hydraulic jack 93 and will move axially upward relative to the second hollow body 95. The lower end 90b of the first hollow body 90 will no longer be abutted by the upper end 95a of the second hollow body 95, but the alignment of the first hollow body 90 is maintained by the third hollow body 98.

In FIGS. 9 to 14, the first hub member 92 and the second hub member 97 are respectively depicted as being conical shaped. The working or the functionality of the apparatus according to the second embodiment of the invention is however, not restricted to the first and second hub members having a conical shape. The first and second members may in fact be envisioned as having a pyramidal shape in a variant of the second embodiment.

As in the description of the first embodiment of the invention which concerns close ended driven piles and close ended injection piles, two or more open ended driven piles or open ended injection piles may similarly be spliced together to form a longer pile, depending on the load bearing requirements.

The bi-directional load testing of open ended driven piles or open ended injection piles which have been spliced together is accomplished by attaching a unit of the apparatus according to the second embodiment of the invention between a pair of piles which are to be combined to form a pile of greater length. The method involves the following steps:

a) Attaching the lower end of a first open ended driven pile or injection pile to the upper end of the first hollow body by welding or other mechanical means.

b) Attaching the upper end of a second open ended driven pile or injection pile to the lower end of the second body by welding or other mechanical means.

c) Connecting a hydraulic line or hose to the hydraulic connection of the hydraulic jack housed in the enclosure of the apparatus, and then pressure testing the hydraulic jack to ensure it is functioning.

d) Driving or injecting the first driven pile or injection pile, the apparatus and the second driven pile or injection pile into the ground.

e) Pressurizing the hydraulic jack to simulate the loads to be tested, and obtaining the corresponding load test data.

As with the method of using the apparatus according to the first embodiment of the invention, method steps a) and b) described above are also interchangeable, and the order of the steps would be dictated by the user's practice or requirements.

If the pressure testing indicates or detects a hydraulic failure or leak in the hydraulic jack at step c), the defective apparatus is detached and replaced, and the replacement apparatus is then subject to the same pressure testing procedure.

The method for carrying out bi-directional load testing of open ended driven piles and injection piles described above may also be used in cases where more than two piles are spliced together to form a longer pile. In such cases, a unit of the apparatus is attached between pairs of spliced piles if load test data from individual splice positions along the longer pile are required.

The present invention is not limited to the embodiments described here, as the description serves only to exemplify the invention and possible variations and further modifications are readily apparent without departing from the scope of the invention.

The invention claimed is:

1. An apparatus for carrying out bi-directional load testing of close ended driven piles and injection piles utilizing a hydraulic jack (13) comprising: an enclosure (1) for housing the hydraulic jack (13) including:
a first hollow body (10) having an upper end (10a) and an open lower end (10b), the upper end being capped by an attached top plate (11) having an external surface (11a) which a lower end (82b) of a first pile (82) may be axially attached to, and an internal surface (11 b), the open lower end (10b) having a cut-out (12) originating on the edge of the open end of the first hollow body for receiving a hydraulic connection (14) for the jack, and
a second hollow body (15) capable of housing the hydraulic jack (13), the second hollow body having an open upper end (15a), and a lower end (15b), the lower end being capped by an attached base plate (17) having an external surface (17a) which an upper end (81a) of a second pile (81) may be axially attached to, and an internal surface (17b) for attaching a base (13a) of the hydraulic jack (13), an opening (16) on the capped lower end (15b) originating at a point where the edge of the lower end abuts the base plate for receiving the hydraulic connection (14) for the jack, and a shield (18) comprising a housing with an open upper end and a wedge-shaped lower end attached to and extending perpendicularly from an edge of the upper surface (17a) of the base plate (17) at a position corresponding to the opening (16) on the second hollow body, wherein the first hollow body (10) and the second hollow body (15) correspond to one another so as to allow axial movement of the first hollow body relative to the second hollow body when actuated by the hydraulic jack (13).

2. The apparatus for carrying out bi-directional load testing of close ended driven piles and injection piles utilizing the hydraulic jack according to claim 1, wherein the first hollow body (10) is axially received by the second hollow body (15) through the open upper end (15a) of the second hollow body.

3. The apparatus for carrying out bi-directional load testing of close ended driven piles and injection piles utilizing the hydraulic jack according to claim 1, wherein the hydraulic jack (13) is a capsule jack.

4. The apparatus for carrying out bi-directional load testing of close ended driven piles and injection piles utilizing the hydraulic jack according to claim 1, wherein the second hollow body (15) is also capable of housing a load cell which is stacked on top of the hydraulic jack (13).

5. The apparatus for carrying out bi-directional load testing of close ended driven piles and injection piles utilizing the hydraulic jack according to claim 1, wherein an extensor meter is attached to the apparatus between the top plate (11) of the first hollow body (10) and the base plate (17) of the second hollow body (15).

6. The apparatus for carrying out bi-directional load testing of close ended driven piles and injection piles utilizing the hydraulic jack according to claim 1, wherein the apparatus is intended for use with cylindrical piles or pipe piles, and the enclosure is cylindrical, hexagonal or octagonal in cross-section.

7. The apparatus for carrying out bi-directional load testing of close ended driven piles and injection piles utilizing the hydraulic jack according to claim 1, wherein the apparatus is intended for use with square piles or H-piles, and the enclosure is square in cross-section.

8. The apparatus for carrying out bi-directional load testing of close ended driven piles and injection piles utilizing the hydraulic jack according to claim 1, wherein the apparatus is intended for use with triangular piles, and the enclosure is triangular in cross-section.

9. A method for carrying out bi-directional load testing of close ended driven piles and injection piles using the apparatus according to claim 1, comprising the steps of:
 a) attaching the upper end (81a) of the second close ended driven pile or injection pile to the external surface (17a) of the base plate (17) of the second hollow body (15),
 b) attaching the lower end (82b) of the first close ended driven pile or injection pile to the external surface (11a) of the top plate (11) of the first hollow body (10),
 c) connecting a hydraulic line to the hydraulic connection (14) and pressure testing the hydraulic jack (13) housed in the apparatus,
 d) embedding completely the first driven pile or injection pile, the apparatus and the second driven pile or injection pile into the ground, and
 e) pressurizing the hydraulic jack (13) to simulate loads to be tested, and obtaining corresponding load test data.

10. The method for carrying out bi-directional load testing of close ended driven piles and injection piles according to claim 9, wherein the method includes the additional step of embedding the lower end (81b) of the second close ended driven pile or injection pile into the ground, before step a).

11. The method for carrying out bi-directional load testing of close ended driven piles and injection piles according to claim 9, further comprising at least one additional pile and at least one additional apparatus, wherein the first and second piles and the at least one additional pile are spliced to form a longer pile and are being subjected to load testing, and the apparatus and the at least one additional apparatus are attached between pairs of spliced piles of the longer pile to obtain load test data from individual splice positions along the longer pile.

* * * * *